(12) United States Patent
Hanazawa et al.

(10) Patent No.: US 9,079,968 B2
(45) Date of Patent: Jul. 14, 2015

(54) ESTABLISHMENT OF MOTIF COMPRISING ACIDIC AMINO ACID, CAPABLE OF STABILIZING PROTEIN IN CELLS, AND APPLICABLE TO PROTEIN THERAPY, CONTROL OF DIFFERENTIATION/UNDIFFERENTIATION OF CELL AND ANTIBODY THERAPY

(75) Inventors: Shigemasa Hanazawa, Kamakura (JP); Yoshikazu Masuhiro, Fujisawa (JP)

(73) Assignee: NIHON UNIVERSITY, Tokyo (JP)

( * ) Notice: Subject to any disclaimer, the term of this patent is extended or adjusted under 35 U.S.C. 154(b) by 221 days.

(21) Appl. No.: 13/321,381

(22) PCT Filed: Nov. 20, 2009

(86) PCT No.: PCT/JP2009/070081
§ 371 (c)(1),
(2), (4) Date: Feb. 16, 2012

(87) PCT Pub. No.: WO2010/134226
PCT Pub. Date: Nov. 25, 2010

(65) Prior Publication Data
US 2013/0288948 A1 Oct. 31, 2013

(30) Foreign Application Priority Data
May 20, 2009 (JP) .................................. 2009-122552

(51) Int. Cl.
*C07K 14/47* (2006.01)
(52) U.S. Cl.
CPC ......... *C07K 14/4703* (2013.01); *C07K 14/4702* (2013.01); *C07K 14/4705* (2013.01)
(58) Field of Classification Search
None
See application file for complete search history.

(56) References Cited

U.S. PATENT DOCUMENTS

| 7,341,604 | B2* | 3/2008 | Rothe et al. ........................ 8/405 |
| 2010/0035824 | A1 | 2/2010 | Görne | |

FOREIGN PATENT DOCUMENTS

| JP | 2009-514800 | | 4/2009 |
| WO | WO 01/21644 | A2 | 3/2001 |
| WO | WO 2007-042010 | A2 | 4/2007 |
| WO | WO 2008-083678 | A2 | 7/2008 |

OTHER PUBLICATIONS

Brinkerhoff et al ("Terminal modifications inhibit proteolytic degradation of an immunogenic MART27-35 Peptide: Implications for Peptide Vaccines", Int. J. Cancer. vol. 83, p. 326-334 (1999).*
Yi et al. (Molecular Cell 29, 465-476, 2008).*
Ishida et al. (J. Biol. Chem 2005, 280:24642-24648).*
Zhou, Hongyan et al., "Generation of Induced Pluripotent Stem Cells Using Recombinant Proteins," *Cell stem cell*, vol. 4, May 2009, pp. 381-384.
Kloβ, Alexander et al. "The cell-penetrating peptide octa-arginine is a potent inhibitor of proteasome activities," *European Journal of Pharmaceutics and Biopharmaceutics*, vol. 72, No. 1, Nov. 2009, pp. 219-225.
Arakawa, T. et al., "Mechanism for decomposition via proteasome of cell cycle-regulatory transcription factor DP-1; and identification of its decomposition control regions Stabilon and Degron," Nippon Nogei Kagakukai Taikai Koen Yoshishu, vol. 2009, Mar. 2009, p. 301.
Kamiya, Yoshiaki et al., "Mechanisms of autoproteolysis of cell-cycle regulatory transcription factor DP-1 through proteasome," *Journal of Japanese Biochemical Society*, 2008, p. 4P-0404.
Yen, Hsueh-Chi Sherry, et al., "Global protein stability profiling in mammalian cells," *Science*, vol. 322, No. 5903, Nov. 2008, pp. 918-923.
Anbanandam, Asokan, et al., "Molecular basis for proline-and arginine-rich peptide inhibition of proteasome." *Journal of molecular biology*, vol. 384, No. 1, Dec. 2008, pp. 219-227 (17 pages as printed).
Yi, Ping, et al., "Atypical protein kinase C regulates dual pathways for degradation of the oncogenic coactivator SRC-3/AIB1," *Molecular cell*, vol. 29, No. 4, Feb. 2008, pp. 465-476.
International Search Report mailed Jan. 19, 2010 for corresponding International Patent Application No. PCT/JP2009/070081.

\* cited by examiner

*Primary Examiner* — Louise Humphrey
*Assistant Examiner* — Tara Martinez

(57) ABSTRACT

A motif is searched which can inhibit the proteolysis of a protein that has been administered to a cell or an individual. Thus, disclosed is a method for designing/producing a protein having resistance to proteolysis. Specifically disclosed is a motif capable of inhibiting proteolysis, which comprises an amino acid region lying between the $396^{th}$ position and the $410^{th}$ position from the C-terminal of DP-1.

6 Claims, 8 Drawing Sheets

(A)

(B)

(A)

(B)

(A)

(B)

(A)

(B)

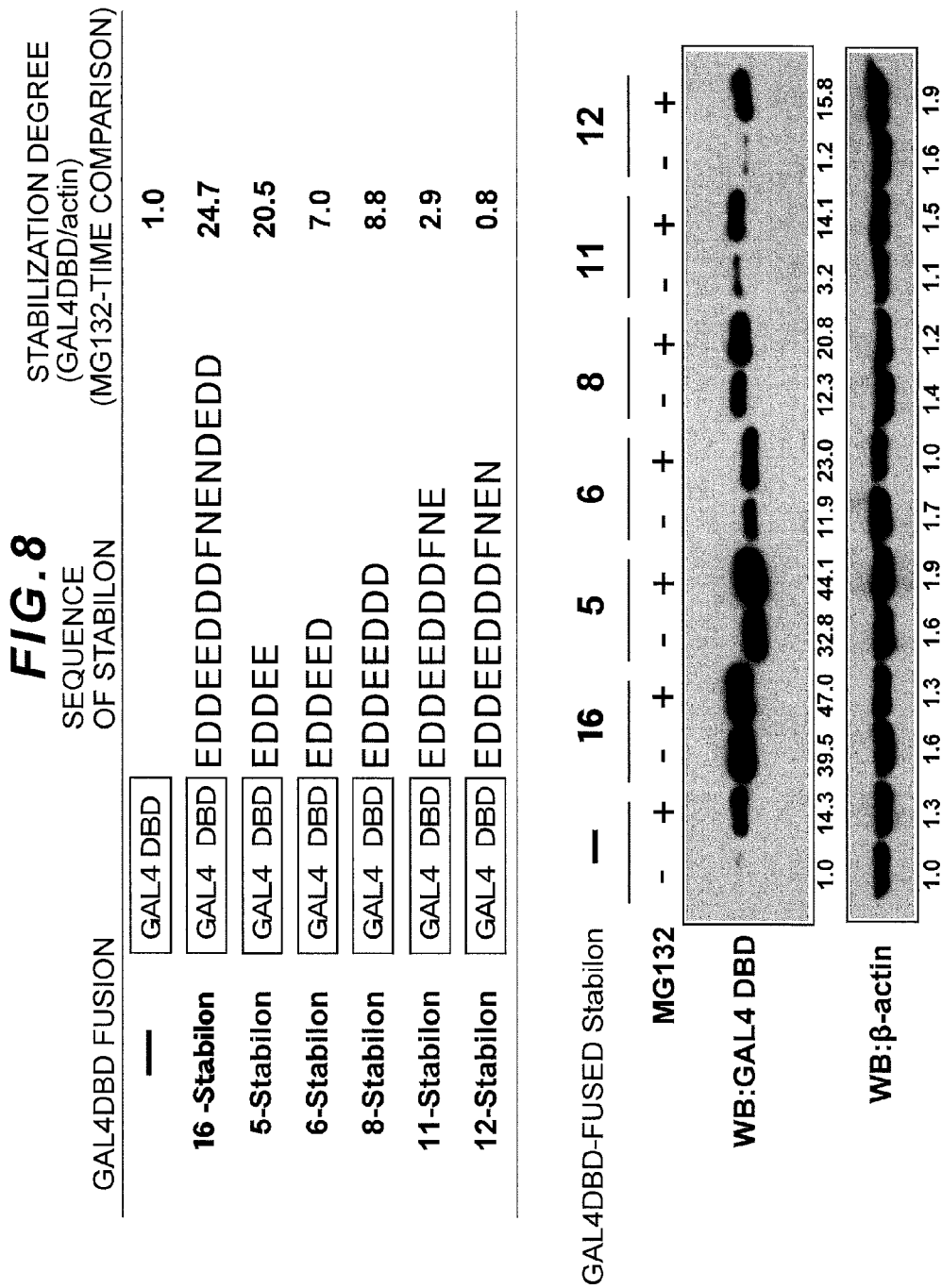

ESTABLISHMENT OF MOTIF COMPRISING ACIDIC AMINO ACID, CAPABLE OF STABILIZING PROTEIN IN CELLS, AND APPLICABLE TO PROTEIN THERAPY, CONTROL OF DIFFERENTIATION/UNDIFFERENTIATION OF CELL AND ANTIBODY THERAPY

CROSS REFERENCE TO RELATED APPLICATIONS

This application claims the benefit under 35 U.S.C. Section 371, of PCT International Application No. PCT/JP2009/070081, filed Nov. 20, 2009, which claimed priority to Japanese Application No. 2009-122552, filed May 20, 2009 in the Japanese Patent Office, the disclosures of which are hereby incorporated by reference.

TECHNICAL FIELD

The present invention relates to an acidic amino acid motif capable of inhibiting the degradation of an administered protein through the fusion of the motif with a protein or an antibody used in protein therapy or antibody therapy.

BACKGROUND ART

Development of protein therapy based on the application of cell membrane-permeable proteins has recently attracted considerable attention. As protein therapy, there is a method of constructing and administering a normal-type protein using an expression system, against a disease caused due to occurrence of abnormality, such as substitution or mutation, in amino acid sequences, resulting from frame shift or the like through the mutagenesis or recombination of a specific gene. Further, as shown in the recently reported construction of protein-induced pluripotent stem (piPS) cells, for induction of undifferentiated cells from already differentiated cells, there is a method of inducing undifferentiation by administering a cell membrane-permeable functional protein (4 types of transcription factors, Oct4, Klf4, Sox2, and cMyc) (for example, see Non-Patent Document 1).

Further, there is a need in regenerative medicine for the establishment of a method for differentiating a specific cell from undifferentiated cells, but it is also highly likely that a cell membrane-permeable protein will need to be applied thereto. Further, antibody therapy of inhibiting the function of a specific protein using an antibody is rapidly under development.

Conventionally, iPS cells have been established by introducing genes of 4 factors (Oct3/4, Sox2, Klf4, and c-Myc) into somatic cells, by means of a viral vector such as a retrovirus or lentivirus, but there has been concern about the risk of oncogenesis due to the insertion of a viral vector into a genome. In addition, the construction of a viral vector requires strictly controlled conditions which have been obstacles in the propagation of iPS cell techniques.

Accordingly, that a piPS cell can be produced by linking 11 arginines as a basic amino acid to 4 factors, modifying the linking product to have cell membrane permeability, and introducing the modified product into a mouse embryonic cell without using a virus has been published.

However, such a protein-based therapy has a disadvantage in that when a protein is administered to a cell or an individual, the protein is degraded by proteasome or phagosome, autophagy or proteolytic enzymes, or the like and, as a result, the administered protein may not particularly work, and may require very frequent administration (for example, see Non-Patent Document 1).

Currently, as a motif capable of inhibiting intracellular proteolysis of such a cell membrane-permeable protein, a poly-arginine tag is known. This is that 8R consisting of 8 arginines or a motif consisting mainly of arginine inhibits proteasomal proteolysis or the like (for example, see Non-Patent Documents 2 and 3).

Further, although it has been reported that an acidic amino acid motif is important for the stability of a protein (for example, see Non-Patent Documents 4 and 5), there is no report showing that an acidic amino acid motif is involved in the inhibition of proteolysis.

Even when an arginine-linked inducer is supplied to a piPS cell, since the inducer is susceptible to proteolysis, there are problems in that long-term administration of an inducer at a high volume into a cell should be made and the construction of a piPS cell takes a long period of several months.

Non-Patent Document 1: Zhou H. et al., Cell Stem Cell. 2009; 4(5): 381-384

Non-Patent Document 2: Kloss A. et al., Eur J Pharm Biopharm. 2009; 72(1): 219-225.

Non-Patent Document 3: Anbanandam A. et al., J Mol. Biol. 2008; 384(1): 219-227.

Non-Patent Document 4: Yi P. et al., Mol. Cell. 2008; 29(4): 465-476.

Non-Patent Document 5: Yen H C. et al., Science. 2008; 322(5903): 918-923.

SUMMARY OF THE INVENTION

Problems to be Solved by the Invention

Therefore, the present invention is to provide a method for designing/producing a proteolysis-resistant protein, by searching for a motif which can inhibit the degradation of a protein administered to a cell or an individual, by proteasome or autophagy, other proteolytic enzymes or the like.

Means for Solving the Problems

As a result of intensive research to address the above-mentioned problems, the inventors of the present invention have discovered that the C-terminal acidic region of a cell cycle-regulatory transcription factor DP-1 is a motif which has resistance to intracellular proteolysis of DP-1 and also strongly inhibits the proteolysis of other molecules. The present invention has been completed based on these findings.

That is, the present invention is directed to a proteolysis-inhibiting motif having a sequence consisting mainly of acidic amino acids, and preferably a proteolysis-inhibiting motif consisting of or including an entire or partial amino acid sequence of the C-terminal acidic amino acid region of a DP-1 protein.

An embodiment of the proteolysis-inhibiting motif in accordance with the present invention is a proteolysis-inhibiting motif consisting of an amino acid region lying between the 395th position and the 410th position from the C-terminal of the DP-1 protein, specifically a proteolysis-inhibiting motif consisting of the following amino acid sequence.

(1) EDDEEDDDFNENDEDD (2) EDDEE

E: glutamic acid
D: aspartic acid
N: asparagine
F: phenylalanine

Another embodiment of the present invention is a proteolysis-inhibiting motif in which the acidic amino acids consist mainly of glutamic acid or aspartic acid.

Further, the present invention is directed to a fusion protein which has acquired proteolysis resistance, by the above-mentioned motif being fused to at least one of the N-terminal, the C-terminal, and a position therebetween of a protein.

As such a protein, there is an inducer for inducing a somatic cell into an induced pluripotent stem cell (iPS cell). Specific examples thereof include an amino acid sequence in which the above-mentioned motif is fused to the C-terminal of Sox2, an amino acid sequence in which the above-mentioned motif is fused to the N-terminal of Oct4, and an amino acid sequence in which the above-mentioned motif is fused to the N-terminal of Klf4.

Further, the present invention is directed to a nucleic acid encoding the amino acid sequence of the above-mentioned motif, an expression vector having the same nucleic acid, and a transformant containing the same expression vector.

Further, the present invention is directed to a pharmaceutical composition containing the above-mentioned fusion protein, a cell membrane-permeable protein having a cell membrane-permeable tag further fused thereto, and an antibody protein containing the same fusion protein or the same cell membrane-permeable protein.

Advantageous Effects of the Invention

The foregoing acidic amino acid motif inhibits the proteolysis of a fused protein. Therefore, since a proteolysis-resistant protein can be provided by fusing the foregoing motif to a cell membrane-permeable protein or antibody used in protein therapy or antibody therapy, utility is exerted such as bringing about remarkable effectiveness (decreased frequency of administration, and enhanced effects) into such a therapy.

Further, since the acidic amino acid motif in accordance with the present invention inhibits the proteolysis of a fused protein, where an expression system for a fusion protein with a desired protein is constructed by introducing a motif-encoding oligonucleotide into an expression plasmid or the like, a protein whose functional analysis has been intensely difficult hitherto due to proteolysis also acquires proteolysis resistance, whereby a functional analysis of the protein becomes possible and the resulting protein is very useful as a tool of molecular biology.

BRIEF DESCRIPTION OF THE DRAWINGS

FIG. 8 is a view illustrating an effect of a change in the sequence of Stabilon on the proteolysis-inhibitory property.

MODE FOR CARRYING OUT THE INVENTION

Figure 1:
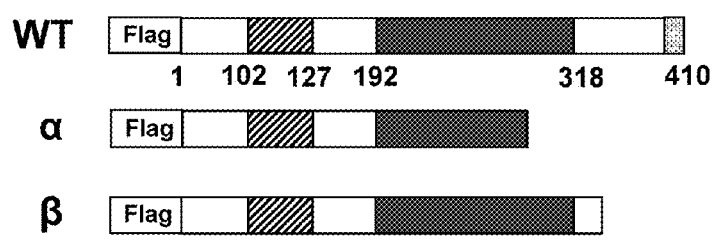
FIG. 1 is a view showing that the C-terminal of DP-1 serving as the trigger of the present invention has an inhibitory function against proteolysis.
Figure 1:
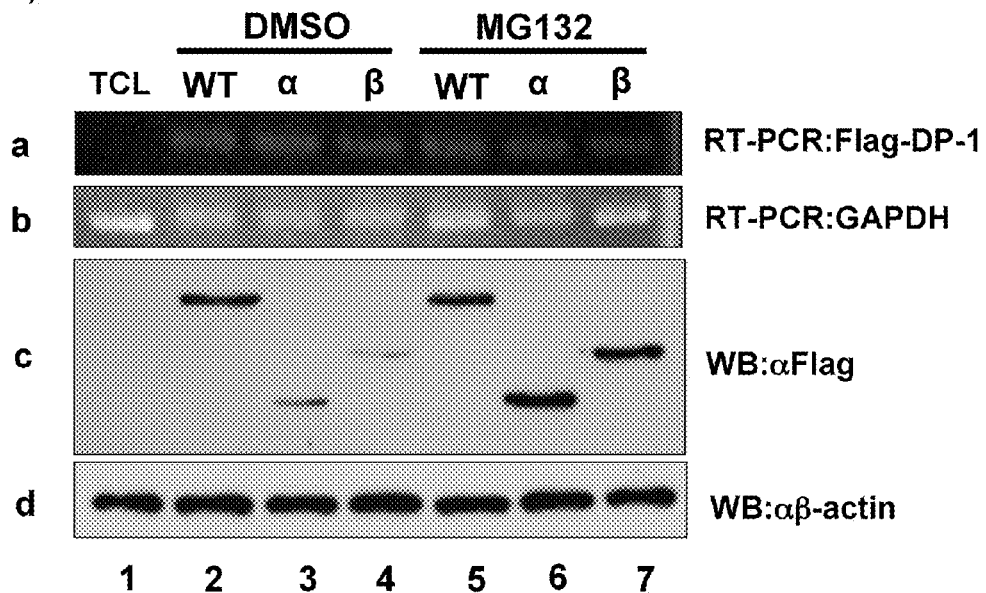

The DP-1 protein consists of 410 amino acids, and the sequence thereof is as follows. The underlined portion is a C-terminal acidic amino acid region of the DP-1 protein, which constitutes the proteolysis-inhibiting motif.

```
makdagliea ngelkvfidq nlspgkgvvs lvavhpstvn plgkqllpkt fgqsnvniaq qvvigtpqrp aasntlvvgs phtpsthfas qnqpsdsspw sagkrnrkge kngkglrhfs mkvcekvqrk gttsynevad elvaefsaad nhilpnesay dqknirrrvy dalnvlmamn iiskekkeik wiglptnsaq ecqnleverq rrlerikqkq sqlqelilqq iafknlvqrn rhaeqqasrp pppnsvihlp fiivntskkt vidcsisndk feylfnfdnt feihddievl krmgmacgle sgscsaedlk marslvpkal epyvtemaqg tvggvfitta gstsngtrfs asdltngadg mlatssngsq ysgsrvetpv syvgeddeed ddfnendedd
```

The above sequence is registered in United States NCBI (National Center for Biotechnology Information) (NM_007111).

The motif consisting mainly of acidic amino acids in accordance with the present invention is a motif consisting mainly of glutamic acid (Glu; E) and aspartic acid (Asp; D), and the composition ratio or length of the motif is not specifically defined and the motif may contain other amino acid residues in its entirety. Further, the motif may contain slightly acidic glutamine (Q; Gln), asparagine (Asn; N), and cysteine (Cys; C). Further, since phosphorylated amino acids (serine [Ser; S], threonine [Thr: T], and tyrosine [Tyr; Y]) also become acidic, the motif may contain these phosphorylated amino acids. Further, an example of the motif in accordance with the present invention is preferably a motif consisting of 1 to 50 amino acids, particularly with the number of acidic amino acids being 20% or more. The motif of the present invention may contain a non-acidic amino acid such as phenylalanine [Phe; F], as long as it has resistance to proteasomal degradation.

As used herein, the term "amino acid" is used in the broadest sense and is intended to encompass naturally-occurring amino acids as well as non-naturally-occurring amino acids such as amino acid variants and derivatives. In a preferred embodiment, the amino acids contained in the acidic amino acid motif of the present invention consist only of naturally-occurring amino acids.

In the present specification, when the expression "one or several amino acids were deleted, substituted or added" is used, the number of amino acids to be substituted is not particularly limited as long as the resulting protein retains the activity of a fused protein, but is in a range of 1 to 9, preferably 1 to 5, and more preferably 1 to 3, or is within 20% of the entire length, and preferably within 10%. The amino acids to be substituted or added may be naturally-occurring amino acids, non-naturally-occurring amino acids or amino acid analogs, and are preferably naturally-occurring amino acids.

The acidic amino acid motif of the present invention (which may be also referred to as "stabilization-promoting region" "Stabilon", "CTAD; C-terminal acidic domain", or "acidic amino acid region") is not particularly limited in terms of its constituent amino acids or length, position or manner of fusion, or the like, as long as it is capable of inhibiting proteolysis of a fused protein.

The acidic amino acid motif of the present invention may be positioned at any site of a fusion protein, and may be linked to the N-terminal, the C-terminal or any internal site of a fusion protein.

There is no particular limitation on the protein to which the proteolysis-inhibiting motif in accordance with the present invention is fused or added, as long as it is a protein which exhibits proteolysis resistance through the addition of a proteolysis-inhibiting motif and which has or is expected to have a certain physiological activity. For example, the foregoing Oct3/4, Sox2, Klf4, and c-Myc are very suitable examples of the protein concerned.

The "nucleic acid encoding the fusion protein in accordance with the present invention" in accordance with the present invention may be any nucleic acid, as long as it contains a base sequence encoding the fusion protein in accordance with the present invention, and is preferably DNA. Such DNA may be obtained from, for example, a genomic DNA, a genomic DNA library, or a cDNA and cDNA library derived from a certain cell or tissue, or otherwise may be a synthetic DNA. Such DNA may be obtained by adjusting a total RNA or mRNA fraction from a certain cell or tissue, followed by RT-PCR amplification.

The nucleic acid encoding the acidic amino acid motif in accordance with the present invention is sequenced based on the amino acid sequence and consists of DNA synthesized based on this sequence. Further, a nucleic acid encoding a protein or peptide being fused to the acidic amino acid motif of the present invention, for example, may be obtained from a cDNA or cDNA library which is obtained according to an RT-PCR method, using an RNA extracted from cells, or otherwise may be synthetic DNA. Individual nucleic acids may be linked and then inserted into an expression vector. Alternatively, individual nucleic acids may be linked such that a fusion protein is expressed, by inserting the nucleic acids into cloning sites of an expression vector. Both cases are included in the "nucleic acid encoding the fusion protein" in accordance with the present invention.

The term "linked such that a fusion protein is expressed" as used herein means in-frame linking of a nucleic acid encoding a motif or the like capable of inducing intracellular localization such as a tag for purification, or a nuclear localization signal (hereinafter, also referred to as "NLS") other than a desired protein, and the acidic amino acid motif of the present invention.

The "expression vector" in accordance with the present invention is a vector into which the above-mentioned nucleic acid encoding the acidic amino acid motif in accordance with the present invention is inserted. The expression vector may be any vector, as long as it satisfies the conditions that the vector exhibits a self-renewal potential in a host, has a phenotypic gene allowing for easy distinctiveness from a host cell, and at least one restriction enzyme cleavage site, and is incapable of surviving outside a host cell. The expression vector may be selected in combination with a host. For example, when the host is *Escherichia coli*, a plasmid such as a pBR-based vector, a pUC-based vector, a pET-based vector, or a pQE-based vector is preferably used as the expression vector. In addition, a plasmid for the expression of animal cells, a plasmid for the expression of *Escherichia coli* cells, a plasmid for the expression of yeast cells, a virus for the expression of insect cells (baculovirus or the like), a viral vector, a phage vector, a cosmid vector, a yeast-derived plasmid, a yeast artificial chromosome (YAC), or the like may also be used as the expression vector.

A promoter functional in a host is incorporated into an expression vector, and the nucleic acid of the present invention is inserted under the control of a promoter. Into an expression vector, for example, a replication origin, a terminator region, a selection marker gene for the selection of a transformant, or the like may be inserted. As the selection marker gene, for example, a gene conferring resistance to an antibiotic, such as tetracycline, ampicillin, kanamycin, neomycin, or geneticin, is used.

The "transformant" in accordance with the present invention refers to a host which is transformed using an expression vector into which the foregoing nucleic acid encoding the acidic amino acid motif in accordance with the present invention is inserted. When the expression vector is an expression vector for *Escherichia coli*, for example, *Escherichia coli*, or other bacteria may be used as the host. The host is preferably *Escherichia coli* since it is also suitable in terms of mass production. When the expression vector is an expression vector for animal cells, for example, cultured cells may be used such as HEK293 cells, HeLa cells, MCF-7 cells, or Cos cells.

Then, a method for producing the fusion protein in accordance with the present invention will be described. The protein to which the acidic amino acid motif of the present invention is fused may be obtained by transforming a host using the foregoing expression vector containing the nucleic acid of the present invention, culturing the host to express a fusion protein, and purifying the fusion protein. Alternatively, the expression may also be transiently investigated by introducing an expression vector into an animal cultured cell using a transfection reagent, electroporation, or the like.

As the method of transforming a host with the expression vector of the protein to which the acidic amino acid motif of the present invention is fused, a known method may be used. For example, mention may be made of a method in which, when the host is *Escherichia coli*, *Escherichia coli* is treated with manganese chloride or calcium chloride to construct a competent cell, an expression vector is mixed in a suspension, and a transformant is harvested by heat shock, an electroporation method, a method in which, in the case of a phage vector, a host is infected with phages, or other methods. In addition, when the host is an animal cultured cell, a transformant may be harvested by a commercially available transfection reagent, an electroporation method, a calcium chloride precipitation method, or the like.

A desired fusion protein may be expressed by culturing the resulting transformant in a suitable medium. The culture conditions, such as culture medium composition, culture temperature and time, and addition of inducers, may be determined according to a known method by those skilled in the art, in such a manner that the transformant grows and efficiently produces a fusion protein. Further, for example, when an antibiotic resistance gene as a selection marker is incorporated into an expression vector, a transformant may be selected by adding an antibiotic to a culture medium.

The resulting fusion protein may be purified by a known method. For example, a host is suspended in a buffer and then disrupted by a method such as ultrasonic fragmentation. Subsequently, when a tag for purification is fused to the fusion protein, through an affinity column having a specific affinity for the tag for purification, the fusion protein adsorbed to the column may be purified by eluting the adsorbed protein using a buffer for elution. In addition, the resulting fusion protein solution may be repeatedly passed several times through an affinity column, such that the degree of purity is further enhanced.

In particular, when the protein to which the acidic amino acid motif of the present invention is fused is used as a medicine, the protein with purity of at least 90%, preferably 95% or more, more preferably 98% or more, and even more preferably 99% or more is preferably used. When the tag for purification to which the acidic amino acid motif of the present invention is fused is incorporated, the above-specified purity can be easily achieved.

For an expression system in *Escherichia coli*, when polyhistidine (His6) is used as a tag for purification, it is also preferred that an expression protein is expressed in the form of an inclusion body and, prior to being passed through an affinity column, is then treated with a protein denaturant such as urea or guanidine hydrochloride, or a surfactant. The denatured and purified protein may be rendered to relevantly function through refolding. The refolding may be carried out, for example, by dilution with or dialysis against a buffer containing an excess amount of arginine.

The protein to which the acidic amino acid motif of the present invention is fused may become a pharmaceutical composition depending on the function of the fused protein.

Examples of the protein to which the acidic amino acid motif of the present invention is fused include a cell membrane-permeable protein, an antibody, a peptide, and a protein undergoing intracellular proteolysis.

When such a protein is subjected to a situation such as intracellular or intra-individual proteolysis, the protein to which the acidic amino acid motif of the present invention is not fused undergoes rapid degradation, whereas it is expected that the protein to which the acidic amino acid motif of the present invention is fused exhibits proteolysis resistance and therefore is recalcitrant to degradation. Accordingly, with regard to a therapy or cell differentiation method requiring long-term, high-dose administration of a protein, when the protein to which the acidic amino acid motif of the present invention is fused is used, it is expected that a very strong effect will be obtained with low-dose administration of a protein in a short period of time.

The pharmaceutical composition containing the protein to which the acidic amino acid motif of the present invention is fused is formulated in the form of a conventional pharmaceutical composition, using a commonly used diluent or excipient, such as a filler, an extender, a binder, an antiwetting agent, a disintegrant, a surface active agent, or a lubricant. Examples of the pharmaceutical composition include a tablet, a pill, a powder, a solution, a suspension, an emulsion, a granule, a capsule, a suppository, and an injection.

The amount of the protein fused with the acidic amino acid motif of the present invention contained in a pharmaceutical composition is not particularly limited and may be appropriately selected from within a broad range. Usually, the content of the protein fused with the acidic amino acid motif of the present invention in a pharmaceutical composition is preferably in a range of 1 to 70% by weight. The pharmaceutical composition, containing the protein fused with the acidic amino acid motif of the present invention as an active ingredient, may also further contain another active ingredient, and may be used in combination with a pharmaceutical composition containing another active ingredient.

There is no particular limitation on the method of administrating the pharmaceutical composition in accordance with the present invention. Administration of the pharmaceutical composition varies depending on various dosage forms, the age and sex of the patient, condition of the disease, and other factors. As a method of administrating a tablet, a pill, a solution, a suspension, an emulsion, a granule and a capsule, for example, mention may be made of oral administration. An injection may be administered alone or in admixture with a common fluid replacement such as glucose or amino acids, via an intravenous, intramuscular, intradermal, subcutaneous or intraperitoneal route. A suppository is intrarectally administered.

A dose of the pharmaceutical composition may be appropriately selected depending on dose regimen, the age and sex of the patient, severity of the disease, and other factors. For oral administration, the protein fused with the acidic amino acid motif of the present invention is usually administered in an amount of about 0.1 mg to 100 mg, preferably about 1.0 to 50 mg, and more preferably about 1.0 to 20 mg, for an adult (60 kg), in each administration. When the pharmaceutical composition is administered as an injection, the protein fused with the acidic amino acid motif of the present invention is administered in an amount of about 0.1 mg to 30 mg, preferably about 0.1 to 20 mg, and more preferably about 0.1 to 10 mg, for an adult (60 kg), in each administration.

The administration frequency of the pharmaceutical composition may be appropriately selected depending on dose regimen, the age and sex of the patient, severity of the disease, and other factors. For example, the pharmaceutical composition may be administered at a frequency of such as once every couple of weeks, once a month, or once every other month.

It is considered that the protein fused with the acidic amino acid motif of the present invention is effective for a protein whose expression is not sufficient and whose functional analysis is impossible, due to undergoing rapid proteolysis in conventional cells, resulting from the expression of the protein in animal cultured cells.

Hereinafter, the present invention will be further described in detail with reference to the following examples. The present invention is by no means limited to the following examples.

Reference is made to FIG. 1. The degradation degree of DP-1, when forced expression of DP-1 (WT, ●, ●) by an expression plasmid is carried out in an HEK 293F cell, was examined in the presence or absence of MG132 which is a proteasome inhibitor.

1.1 Construction and Bulk Adjustment of Expression Plasmid

In order to express Flag-tagged DP-1 (WT, ●, ●) in a mammalian cultured cell, cDNAs encoding a Flag tag and DP-1 were inserted by ligation into a pcDNA3 expression plasmid (Invitrogen) (FIG. 1-A, construction details of this expression plasmid have been reported by Ishida H. et al., 2005 J Biol. Chem. 2005 vol. 280 No. 26: 24642-8).

The Flag tag is an amino acid sequence consisting of Asp-Tyr-Lys-Asp-Asp-Asp-Asp-Lys, and is used from the viewpoint of Western blotting detection becoming very easy (an HRP-conjugated Flag antibody [SIGMA] used in Western blotting is capable of detecting a Flag-tagged protein with very high sensitivity) through the fusion of this sequence.

Individual monoclonalized *Escherichia coli* containing the plasmid were cultured in an LB medium containing ampicillin. The cultured cells were harvested by centrifugation, and then the expression plasmid was purified using a Plasmid Purification MAXI Kit (QIAGEN).

1.2 Cell Culture

HEK 293F cells were cultured in a DMEM containing 10% FBS (and containing penicillin and streptomycin as antibiotics). For transfection, HEK 293F cells were seeded onto a 6 cm dish on the preceding day, such that 50% confluence is achieved upon transfection.

1.3 Transfection

According to combinations arranged as in lanes 1 to 7 of FIG. 1, HEK 293F cells were transfected with the plasmid. Using 200 ng of Flag-DP-1/pcDNA3 as the expression plasmid, a cDNA3 expression plasmid for correction was added to a total of 2.6 mg which was adjusted to make 100 ml by a TE buffer (10 mM Tris-HCl [pH 8.0], 1 mM EDTA). As the transfection reagent, a Polyfect transfection reagent was used. 30 ml of a Polyfect transfection reagent (QIAGEN) was added to the expression plasmid solution, followed by performing stirred suspension. This was followed by standing for 5 minutes to form a DNA,Polyfect transfection reagent complex. During this, the culture medium of cells was exchanged. The DNA,Polyfect transfection reagent complex was added to the medium, followed by slow mixing. The culture medium was placed in a $CO_2$ incubator, and the cell culture was continued under the conditions of 5% $CO_2$ and 37° C.

1.4 Addition of MG132

MG132 was dissolved in DMSO and then used. MG132 was added to lanes 5 to 7, before 6 hours of cell harvest, such that a final concentration of 10 mM was achieved. DMSO alone was added to lanes 2 to 6 such that a DMSO concentration became the same concentration as in lanes 5 to 7.

Expression analysis of mRNA according to an RT-PCR method (FIG. 1, panels a and b)

1.5.1 Extraction of total RNA

The medium was discarded from the 24-hour cultured cells after transfection. 1 ml of PBS was added thereto, and the cells were dissociated by gentle pipetting and transferred to a 1.5 ml Eppendorf tube. The cells were recovered by centrifugation at 1,500 rpm, and the supernatant was decanted. 700 ml of PBS was added to the precipitated cells, and 700 ml of Isogen (Nippon Gene Co., Ltd.) was further added thereto. According to the protocol of Isogen, the total RNA was adjusted.

1.5.2 RT-PCR Method

Quantification of the Flag-DP-1 mRNA derived from Flag-DP-1/pcDNA3 subjected to forced expression was attempted by RT-PCR. Primers for RT-PCR were designed as follows, using a housekeeping gene GAPDH for Flag-DP-1 mRNA and for correction.

```
Flag-DP-1
Forward: AGAGAACCCACTGCTTACTGGCTTATCGAAATTAATAC

Reverse: CGAGCGGGTTGACGGTGGAGGGGTGAACGGCCACG

GAPDH
Forward: CCCAGAAGACTGTGGATGGCCCC

Reverse: CGTTGTCATACCAGGAAATGAGCTTGACAAAG
```

The RT reaction was carried out as follows, using an AccessQuick RT-PCR system (Promega Corporation).

1.5.2.a. RT Reaction Composition
RNA (1 mg/ml): 1 ml
Master Mix (2×): 10 ml
3' primer (50 pmol/l): 0.4 ml
AMV Reverse Transcriptase: 0.4 ml
Nuclease-Free Water: 13 ml
Total: 20 ml 1.5.2.b. RT-PCR Program
45° C., 45 minutes
94° C., 2 minutes
4° C., ∞

The PCR reaction was carried out as follows, using an Ex Taq (Takara Bio Inc.).

1.5.2.c. PCR Reaction Composition
10×Ex Taq Buffer: 4 ml
dNTP Mixture: 3.2 ml
5' primer: 0.8 ml
3' primer: 0.8 ml
TaKaRa Ex Taq (5 units/µl): 0.4 ml
$H_2O$: 30.8 ml
Total: 40.0 ml 1.5.2.d. PCR Reaction Program
Amplification of Flag-pcDNA3-DP-1
96° C., 1 minute
96° C., 20 seconds
71° C., 45 seconds
4° C., ∞
(35 cycles of the reaction at 96° C. for 20 seconds and at 71° C. for 45 seconds were repeated)
Amplification of GAPDH
96° C., 1 minute
96° C., 20 seconds
71° C., 45 seconds
4° C., ∞
(30 cycles of the reaction at 96° C. for 20 seconds and at 71° C. for 45 seconds were repeated)

1.5.2.e. Electrophoretic Confirmation of Amplification

The PCR product was electrophoretically developed using 2% agarose gel, stained with ethidium bromide, and then confirmed by a Transilluminator (Advance Co., Ltd.), followed by recording with a digital camera FinePix F11 (FUJIFILM).

Analysis of protein expression level by Western blotting analysis (FIG. 1, panels c and d)

1.6.1 Total Cell Extract

The medium was discarded from the 24-hour cultured cells after transfection. 1 ml of PBS was added thereto, and the cells were dissociated by gentle pipetting and transferred to a 1.5 ml Eppendorf tube. The cells were recovered by centrifugation at 1,500 rpm, and the supernatant was decanted. 300 ml of NET-N+buffer (20 mM Tris-HCl [pH 7.9], 1 mM EDTA [pH 7.9], 150 mM NaCl, 1% NP-40, and Protease Inhibitor Cocktail were respectively added immediately prior to use) was added to the precipitated cells, followed by extraction with several occasions of pipetting, and centrifugation at 13,500 rpm and 4° C. The supernatant was transferred to another fresh 1.5 ml Eppendorf tube, and 300 ml of 2×SDS-PAGE sample buffer was added thereto, followed by stirring. Boiling was carried out at 98° C. for 1 minute, followed by sampling.

1.6.2 Western Blotting Method 10 ml of a cell extract sample of each lane was loaded on 12% SDS-PAGE gel, followed by electrophoresis. After the electrophoresis was completed, the gel was removed from the gel plate, and dipped in a transfer buffer. The gel was set in a Transfer Blot (BioRad), and the separated sample protein was transferred onto a PVDF membrane (Millipore). The sample protein-transferred PVDF membrane was dipped in a blocking buffer (Nacalai Tesque). After the protein-transferred PVDF membrane was washed four times with a TBST buffer (20 mM Tris-HCl [pH 7.5], 150 mM NaCl, 0.1% Tween 20), a horseradish peroxidase (HRP)-conjugated Flag antibody was used as a primary antibody, and a housekeeping gene b-actin was used to secure homogeneity of the sample extract. When b-actin was used, after the protein-transferred membrane was washed four times with a TBST buffer, an HRP-conjugated anti-mouse IgG antibody was used as a secondary antibody. Color development was detected by a Hyperfilm (GE Healthcare) using Chemi-Lumi One as a substrate for HRP.

In lanes 2 to 7 of panels a and b of FIG. 1, Flag-DP-1 (WT, ●●, ●) mRNA exhibited a nearly equal amount of satisfactory expression. There was no change in the amount of mRNA due to addition of MG132. In DMSO alone-treated group of panels c and d of FIG. 1 (lanes 2 to 4), the Flag-DP-1 (WT) protein exhibited ordinary satisfactory expression (panel c, lane 2), whereas the Flag-DP-1 (●, ●●) protein exhibited a very low level of expression (panel c, lanes 3 and 4). In the MG132-treated group (lanes 5 to 7), the Flag-DP-1 (WT, ●●, ●) protein exhibited a nearly equal amount of expression (panel c, lanes 5 to 7). Accordingly, the Flag-DP-1 (●, ●) protein exhibited a significant increase in expression level due to the addition of MG132 (comparison of lanes 3 and 4 with lanes 6 and 7 in panel c). Accordingly, it was confirmed that the Flag-DP-1(●, ●) protein is a protein being strongly decomposed by proteasome. In addition, it was considered that a domain or motif important for the inhibition of degradation of DP-1 is present in the C-terminal region deficient in Flag-DP-1 (●, ●).

Figure 2:
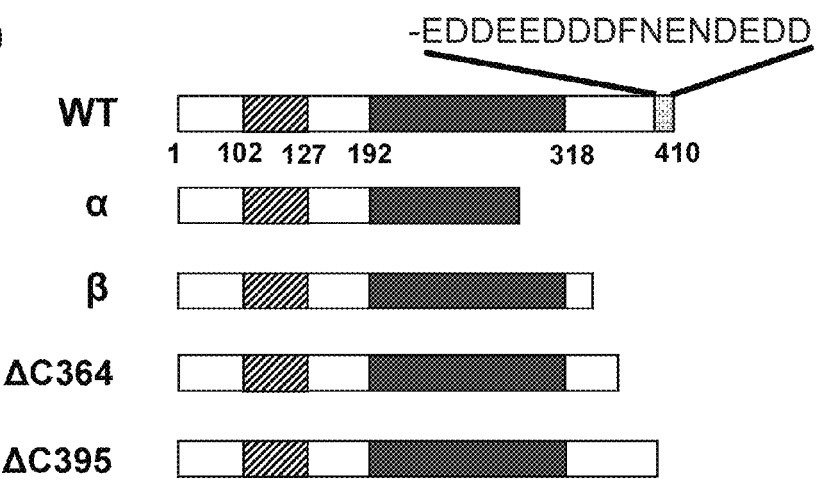
FIG. 2 is a view showing that an amino acid region lying between the 396$^{th}$ position and the 410$^{th}$ position from the C-terminal of DP-1 is a region inhibiting proteolysis of DP-1.
Figure 2:
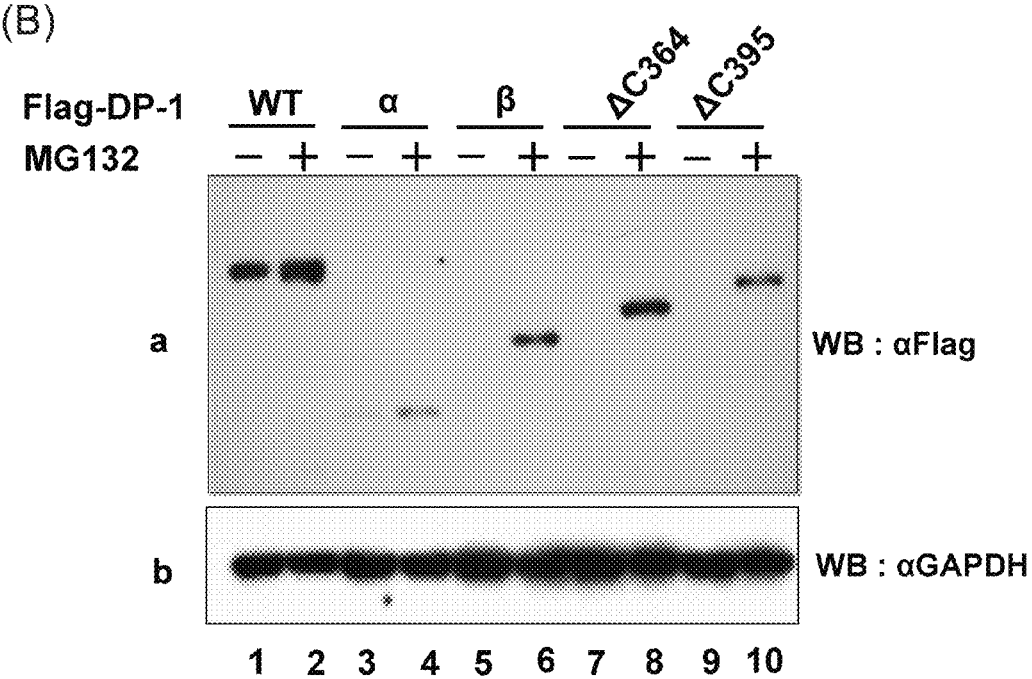

Next, description is made of FIG. 2. The degradation degree of DP-1, when forced expression of DP-1(WT, ●, ●, ΔC364, ΔC395) by an expression plasmid is carried out in an HEK 293F cell, was examined in the presence or absence of MG132 which is a proteasome inhibitor.

2.1 Construction and Bulk Adjustment of Expression Plasmid

In order to express Flag-tagged DP-1 (WT, ●, ●, ΔC364, ΔC395) in a mammalian cultured cell, cDNAs encoding a Flag tag and DP-1 were inserted by ligation into a pcDNA3 expression plasmid (Invitrogen) (FIG. 2-A). Flag-tagged DP-1 (WT, ●●, ●) was the same as in Section 1.1 above. With regard to construction of the Flag-tagged DP-1 (ΔC364, ΔC395) expression plasmid, the DP-1-deficient mutant fragment was amplified by PCR using the following primers.

```
FlagDP-1(Δ C364)
Forward;
5'-TCGAATTCATGGCAAAAGATGCCGGTCTAATTGAA-3'

Reverse;
5'-AATTCTAGATCACAGCTCACTGGCAGAGAACCTIGTG-3'

DP-1(Δ C395)
Forward;
5'-TCGAATTCATGGCAAAAGATGCCGGTCTAATTGAA-3'

Reverse;
5'-AATTCTAGATCACCCCCGACGTAGGACACCGGAGTCTC-3'
```

PCR reaction
50 pmol 5' primer: 1 μl
50 pmol 3' primer: 1 μl
Template DNA (10 ng/μl): 1 μl
5xPS Buffer: 10 μl
dNTP: 4 μl
H$_2$O: 32.5 μl
PrimeStar HS DNA Polymerase: 0.5 μl
Total: 50 μl The mixed liquid was reacted according to the following cycle.
98° C., 1 minute
98° C., 10 seconds
71° C., 1 minute
4° C., ∞
(28 cycles of the reaction at 98° C. for 10 seconds and at 71° C. for 1 minute were repeated)

The amplified product was treated with a restriction enzyme and was inserted by ligation into a pcDNA3-Flag vector treated with the same restriction enzyme. The insertion was confirmed by restriction treatment after a mini-preparation of plasmid DNA. Further, correctness of the entire sequence was confirmed by the sequence.

For bulk adjustment of the expression plasmid, the expression plasmid was purified using a Plasmid Purification MAXI Kit (QIAGEN) as set forth in [0039].

2.2 Details of cell culture are as described in Section 1.2 above, 2.3 Details of transfection are as described in Section 1.3 above, 2.4 Addition details of MG132 are as described in Section 1.4 above, 2.5 Details of Western blotting analysis are as described in Section 1.5 above.

In the absence of MG132, DP-1(●, ●) exhibited nearly no expression (FIG. 2-B, panel a, lanes 3 and 5). In the absence of MG132, DP-1(ΔC364, ΔC395) also exhibited no expression (FIG. 2-B, panel a, lanes 7 and 9), similar to DP-1(●, ●). Further, the degradation of DP-1 (ΔC364, ΔC395) was inhibited by the addition of MG132 (FIG. 2-B, panel a, lanes 8 and 10). Accordingly, it was confirmed that the region inhibiting the proteasomal degradation of DP-1 is a region corresponding to $395^{th}$ to $410^{th}$ amino acids (EDDEEDDDFNEND-EDD) of the endmost C-terminal of DP-1. This region is an acidic region rich in glutamic acid (E) and aspartic acid (D).

Figure 4:
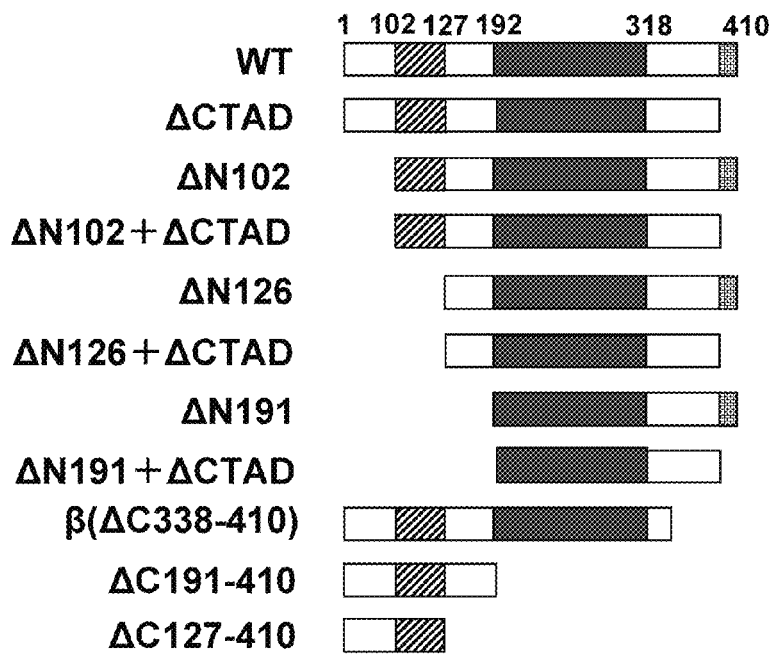
FIG. 4 is a view showing that a proteolysis promotion region of DP-1 is present in a 128$^{th}$ to 192$^{nd}$ amino acid region of DP-1.
Figure 4:
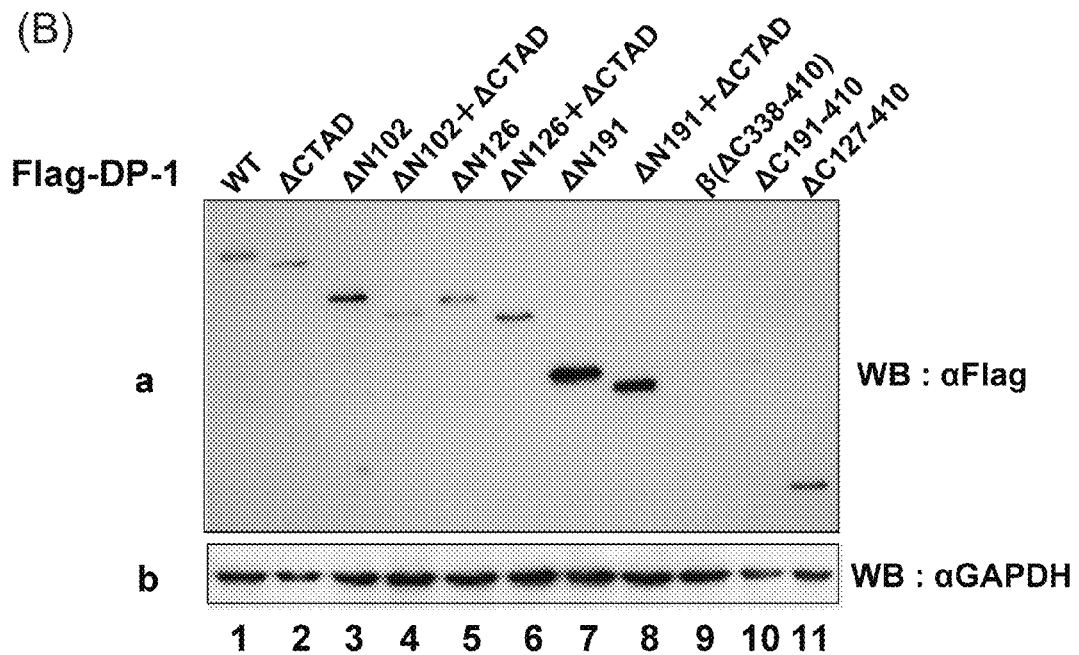

Next, description is made of FIG. 4. The degradation degree of DP-1, when forced expression of DP-1(●, ●+CTAD, ΔC364, ΔC364+CTAD) by an expression plasmid is carried out in an HEK 293F cell, was examined.

3.1 Construction and Bulk Adjustment of Expression Plasmid

Figure 3:
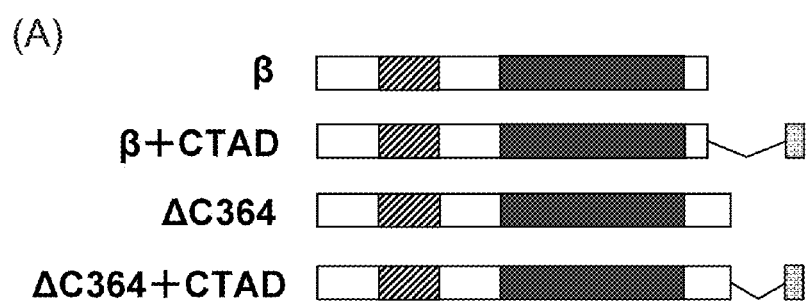
FIG. 3 is a view showing that an amino acid region lying between the 396$^{th}$ position and the 410$^{th}$ position from the C-terminal of DP-1 inhibits proteolysis promotion of DP-1 (●).
Figure 3:
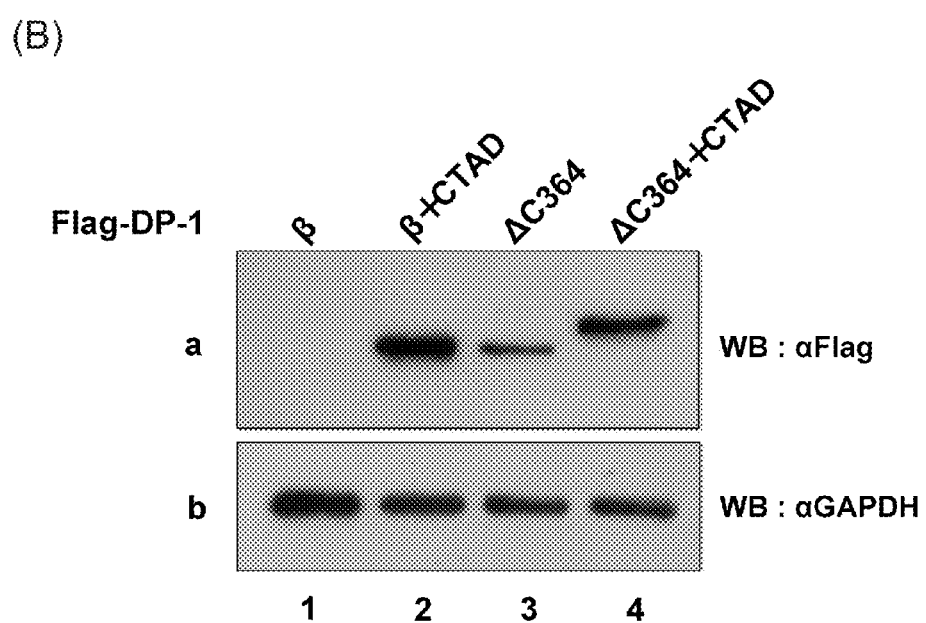

In order to express Flag-tagged DP-1(●, ●+CTAD, ΔC364, ΔC364+CTAD) in a mammalian cultured cell, cDNAs encoding a Flag tag and DP-1 were inserted by ligation into a pcDNA3 expression plasmid (Invitrogen) (FIG. 3-A). Construction details of Flag-tagged DP-1(●) were the same as in Section 1.1 above. Construction details of Flag-tagged DP-1(ΔC364) were the same as in Section 2.1 above. With regard to construction of the Flag-tagged DP-1(●+CTAD, ΔC364+CTAD) expression plasmid, a CTAD-encoding fragment was ligated into DP-1(●) and DP-1(ΔC364), respectively. The insertion was confirmed by restriction treatment after a mini-preparation of plasmid DNA. Further, correctness of the entire sequence was confirmed by the sequence.

For bulk adjustment of the expression plasmid, the expression plasmid was purified using a Plasmid Purification MAXI Kit (QIAGEN) as set forth in Section 1.1 above.

3.2 Details of cell culture are as described in Section 1.2 above, 3.3 Details of transfection are as described in Section 1.3 above, 3.4 Details of Western blotting analysis are as described in Section 1.6 above.

All experiments of FIG. 3 were carried out in the absence of MG132.

Flag-DP-1(●) exhibited nearly no expression (FIG. 3-B, panel a, lane 1). Flag-DP-1(●+CTAD) exhibited sufficient expression (FIG. 3-B, panel a, lane 2). Flag-DP-1(ΔC364) exhibited weak expression (FIG. 3-B, panel a, lane 3). Flag-DP-1(ΔC364+CTAD) exhibited sufficient expression (FIG. 3-B, panel a, lane 4). Accordingly, it was found that the region inhibiting the proteasomal degradation of DP-1 (395th to 410th amino acids of the endmost C-terminal of DP-1, EDDEEDDDFNENDEDD; CTAD) determined in FIG. 2 inhibits a region involved in the proteolysis of DP-1 present in the DP-1(●) region.

Next, description is made of FIG. 4. The degradation degree of DP-1, when forced expression of DP-1(WT, ΔCTAD, ΔN102, ΔN102+CTAD, ΔN126, ΔN126+CTAD, ΔN191, ΔN191+CTAD, ●, ΔC191-410, ΔC127-410) by an expression plasmid is carried out in an HEK 293F cell, was examined.

4.1 Construction and Bulk Adjustment of Expression Plasmid

In order to express Flag-tagged DP-1 (WT, ΔCTAD, ΔN102, ΔN102+ΔCTAD, ΔN126, ΔN126+ΔCTAD, ΔN191, ΔN191+ΔCTAD, ●, ΔC191-410, ΔC127-410) in a mammalian cultured cell, cDNAs encoding a Flag tag and DP-1 were inserted by ligation into a pcDNA3 expression plasmid (Invitrogen) (FIG. 4-A). Construction details of Flag-tagged DP-1 (WT, ●) were the same as in [0039] above. With regard to construction of Flag-tagged DP-1(ΔCTAD, ΔN102, ΔN102+ ΔCTAD, ΔN126, ΔN126+ΔCTAD, ΔN191, ΔN191+ ΔCTAD, ●, ΔC191-410, ΔC127-410), the DP-1-deficient mutant fragment was amplified by PCR using the following primers.

```
FlagDP-1(Δ CTAD)
Forward;
5'-TCGAATTCATGGCAAAAGATGCCGGTCTAATTGAA-3'

Reverse;
5'-AATTCTAGATCACCCCGACGTAGGACACCGGAGTCTC-3'

DP-1(Δ N102)
Forward;
5'-AAGAATTCAAGCGCAACAGGAAAGGAGAGAAGAATG-3'

Reverse;
5'-AATTCTAGATCAGTCGTCCTCGTCATTCTCGTTG-3'

DP-1(Δ N102 + Δ CTAD)
Forward;
5'-AAGAATTCAAGCGCAACAGGAAAGGAGAG AAGAATG-3'

Reverse;
5'-AATTCTAGATCACCCCGACGTAGGACACCGGAGTCTC-3'

DP-1(Δ N126)
Forward;
5'-AAGAATTCCAGAGGAAAGGGACCACTTCCTACAACG-3'

Reverse;
5'-AATTCTAGATCAGTCGTCCTCGTCATTCTCGTTG-3'

DP-1(Δ N126 + Δ CTAD)
Forward;
5'-AAGAATTCCAGAGGAAAGGGACCACTTCCTACAACG-3'

Reverse;
5'-AATTCTAGATCACCCCGACGTAGGACACCGGAGTCTC-3'

DP-1(Δ N191)
Forward;
5'-AAGAATTCGGTCTGCCCACCAACTCGGC-3'

Reverse;
5'-AATTCTAGATCAGTCGTCCTCGTCATTCTCGTTG-3'

DP-1(Δ N191 + Δ CTAD)
Forward;
5'-AAGAATTCGGTCTGCCCACCAACTCGGC-3'

Reverse;
5'-AATTCTAGATCACCCCGACGTAGGACACCGGAGTCTC-3'

DP-1(Δ C191-410)
Forward;
5'-TCGAATTCATGGCAAAAGATGCCGGTCTAATTGAA-3'

Reverse;
5'-TTTCTAGATTAAATCCACTTGATCTCCTTCTTCTCCTTGGAG-3'

DP-1(Δ C127-410)
Forward;
5'-TCGAATTCATGGCAAAAGATGCCGGTCTAATTGAA-3'

Reverse;
5'-TTTCTAGATTACACCTTCTCGCAGACCTTCATGGAGA-3'
```

PCR reaction
50 pmol 5' primer: 1 μl
50 pmol 3' primer: 1 μl
Template DNA (10 ng/μl): 1 μl
5xPS Buffer: 10 μl
dNTP: 4 μl
H$_2$O: 32.5 μl
PrimeStar HS DNA Polymerase: 0.5 μl
Total: 50 μl
The mixed liquid was reacted according to the following cycle.
98° C., 1 minute
98° C., 10 seconds
71° C., 1 minute
4° C., ∞
(28 cycles of the reaction at 98° C. for 10 seconds and at 71° C. for 1 minute were repeated)

The amplified product was treated with a restriction enzyme and was inserted by ligation into a pcDNA3-Flag vector treated with the same restriction enzyme. The insertion was confirmed by restriction treatment after a mini-preparation of plasmid DNA. Further, correctness of the entire sequence was confirmed by the sequence.

For bulk adjustment of the expression plasmid, the expression plasmid was purified using a Plasmid Purification MAXI Kit (QIAGEN) as set forth in 1.1 above.

4.2 Details of cell culture are as described in Section 1.2 above, 4.3 Details of transfection are as described in Section 1.3 above, 4.4 Details of Western blotting analysis are as described in Sections 1.61 and 1.62 above.

All experiments of FIG. 4 were carried out in the absence of MG132.

When Flag-DP-1 (various deficient mutants; as described in Section 4.1 above) was expressed, Flag-DP-1(ΔN191, ΔN191+ΔCTAD) exhibited sufficient expression (FIG. 4-B, panel a, lanes 7 and 8). Flag-DP-1(ΔC191-410) exhibited nearly no expression (FIG. 4-B, panel a, lane 10), whereas Flag-DP-1(ΔC127-410) exhibited expression (FIG. 4-B, panel a, lane 11). Accordingly, it was found that the region promoting proteolysis of DP-1 is a region of from 128th to 192nd amino acids.

Figure 5:
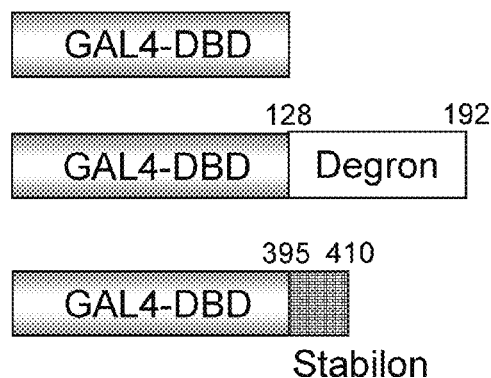
FIG. 5 is a view showing that an amino acid region lying between the 396$^{th}$ position and the 410$^{th}$ position from the C-terminal of DP-1 is capable of inhibiting proteolysis also in other molecules (GAL4 DBD; GAL4DNA binding domain).
Figure 5:
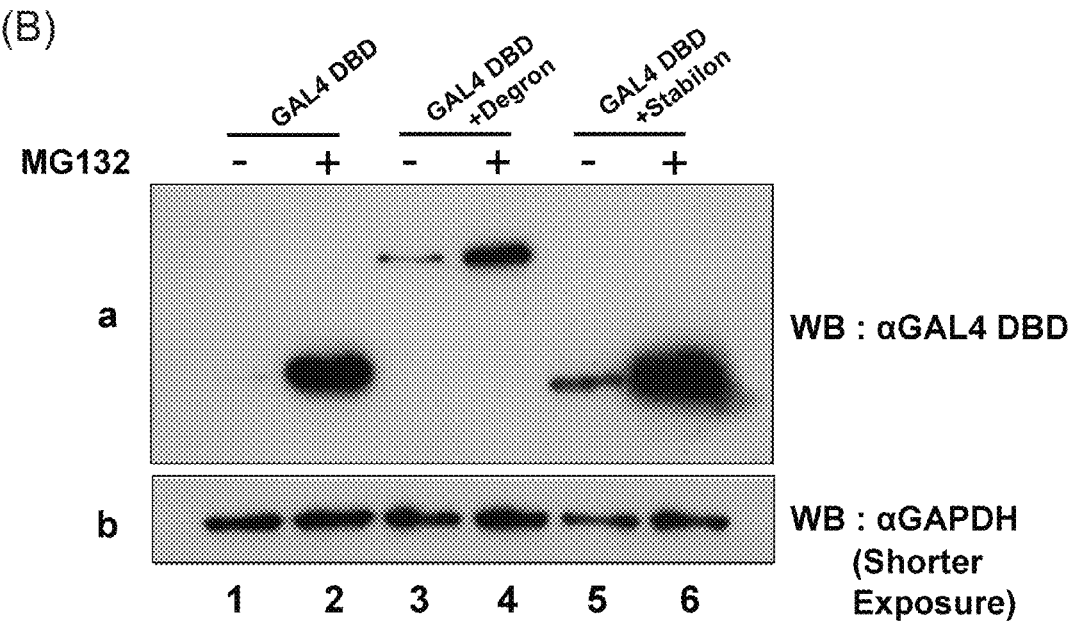

Next, description is given to FIG. 5. In order to confirm whether DP-1 (CTAD) functions to inhibit proteolysis also in other molecules which are susceptible to proteolysis, the degradation degree of DP-1, when DP-1 (CTAD) is fused to a DNA binding domain (also abbreviated as DBD) of GAL4 which is a protein prone to degradation in cells and is then subjected to forced expression in an HEK 293F cell, was examined in the presence or absence of MG132 which is a proteasome inhibitor.

5.1 Construction and Bulk Adjustment of Expression Plasmid

In order to express GAL4 DBD alone, GAL4 DBD-fused DP-1 (Stabilon; CTAD, Degron) in a mammalian cultured cell, cDNAs encoding GAL4 DBD and DP-1 were inserted by ligation into a pcDNA3 expression plasmid (Invitrogen) (FIG. 5-A). With regard to construction of this expression plasmid, a GAL4 DBD-encoding DNA was cleaved from a pM plasmid (Clontech) using BglII-EcoRI, and was inserted into a pcDNA3 digested with a restriction enzyme BamHI-EcoRI. GAL4 DBD-fused Stabilon; CTAD was inserted into the foregoing GAL4 DBD-pcDNA3 through EcoRI-XbaI digestion. GAL4 DBD-fused Degron was inserted into the foregoing GAL4 DBD-pcDNA3 through EcoRI-XbaI digestion.

For bulk adjustment of the expression plasmid, the expression plasmid was purified using a Plasmid Purification MAXI Kit (QIAGEN) as set forth in Section 1.1 above.

5.2 Details of cell culture are as described in Section 1.2 above, 5.3 Details of transfection are as described in Section 1.3 above, 5.4 Addition details of MG132 are as described in Section 1.4 above, 5.5 Details of Western blotting analysis are as described in Sections 1.61 and 1.62 above.

With regard to an antibody for Western blotting, a GAL4 DBD antibody (Santa Cruz; RK5C1; HRP-conjugated; sc-501) was used in the detection of GAL4.

In the absence of MG132, GAL4 DBD exhibited very weak expression (FIG. 5-B, panel a, lane 1). In the absence of MG132, GAL4 DBD+Degron exhibited weak expression (FIG. 5-B, panel a, lane 3). In the absence of MG132, GAL4 DBD+Stabilon (CTAD) exhibited sufficient expression (FIG. 5-B, panel a, lane 5). Further, GAL4 DBD, GAL4DBD+Degron, and GAL4DBD+Stabilon (CTAD) exhibited significantly improved expression by the addition of MG132 (FIG. 5-B, panel a, lanes 2, 4 and 6). Accordingly, CTAD ($395^{th}$ to $410^{th}$ amino acids of the C-terminal of DP-1; EDDEEDDDFNENDEDD) of DP-1 inhibited proteasomal degradation of GAL4 DBD. Therefore, CTAD of DP-1 has a high probability of becoming a general inhibitory motif of proteins prone to proteolysis.

Next, an embodiment will be described in which Stabilon is introduced into an iPS cell inducer.

Experimental Method

Figure 6:
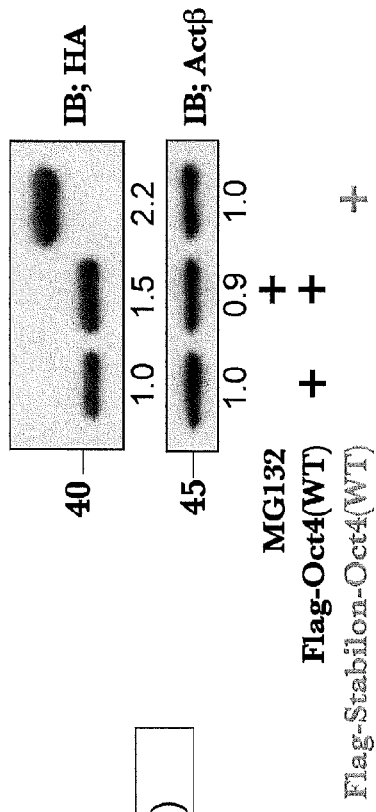
FIG. 6 is a first view illustrating the results of an embodiment with introduction of Stabilon into an iPS cell inducer.
Figure 6:
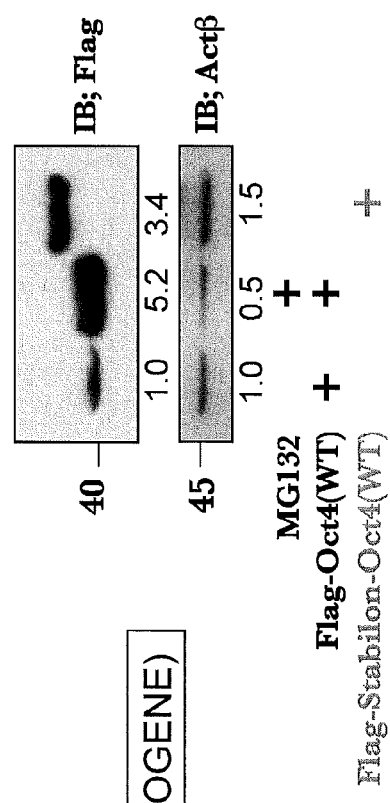
Figure 7:
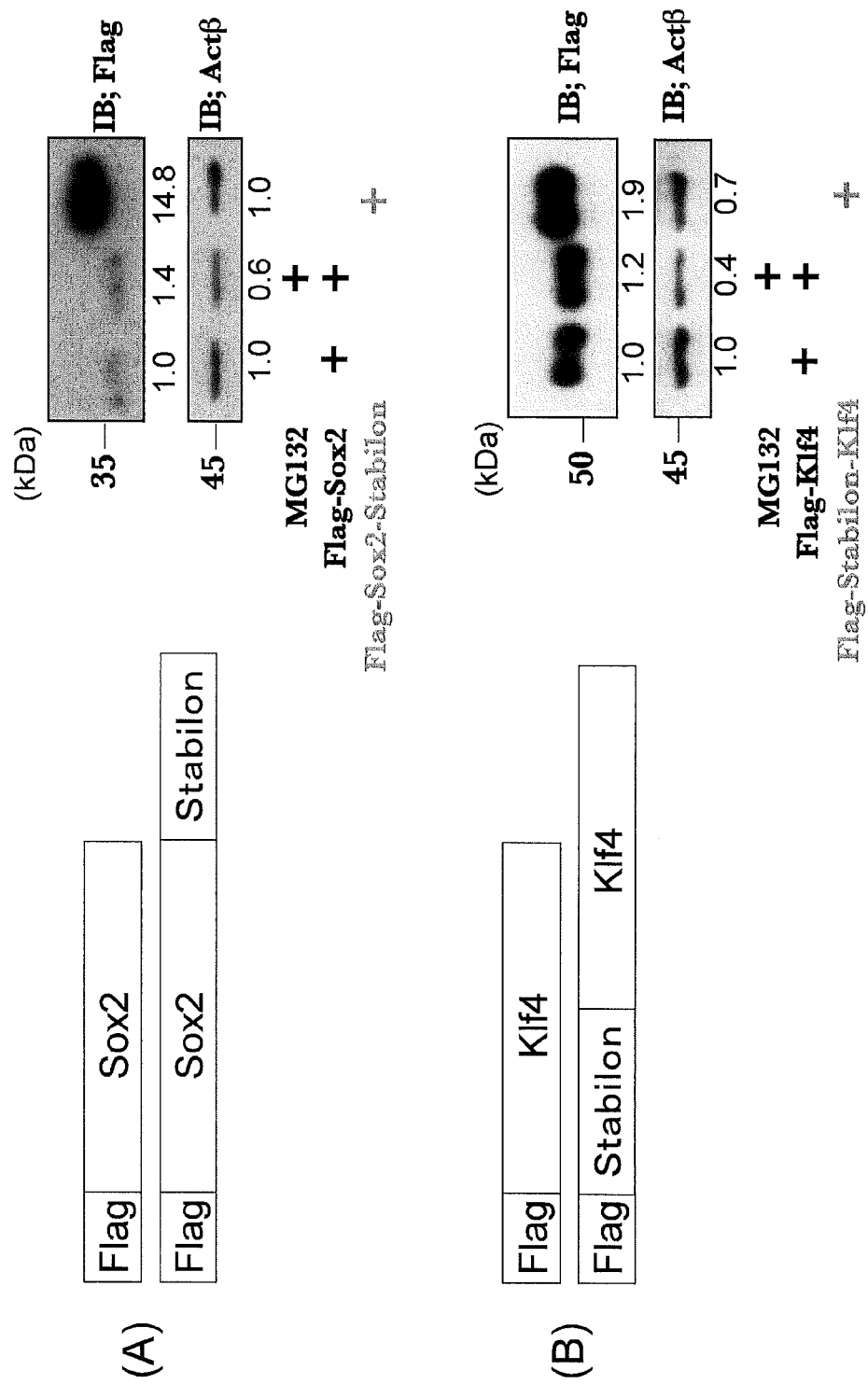
FIG. 7 is a second view illustrating the results of an embodiment with introduction of Stabilon into an iPS cell inducer.

HEK293 cells cultured in a D-MEM containing 10% FBS were transfected with Flag- or HA-tagged Oct4, Sox2 or Klf4 incorporated into a pcDNA3 vector, using Polyfect. After 24 hours of transfection, a proteasome inhibitor MG132 at a final concentration of 10 µM was added to dishes of individual experimental lanes 2. After 36 hours of transfection incubation, the cells were washed with a PBS buffer, and the protein was extracted with a TNE-N+buffer. The extract was equally aliquoted and developed by SDS-PAGE electrophoresis. After the electrophoresis was completed, the separated protein was transferred onto a PVDF membrane and then subjected to Western blotting analysis using an HRP-conjugated Flag antibody and a β-actin antibody. Chemi-Lumi One L (Nacalai Tesque) as a substrate of detection was exposed to a Hyperfilm (GE Healthcare), followed by detection. Quantification of the detected band was carried out using an ImageJ (NIH). Stabilon was fused to N-termini of Oct4 and klf4 and was fused to the C-terminal of Sox2. The results are shown in FIGS. 6 and 7.

Results

HA-Oct4 (WT) was about 1.7-fold stabilized by MG132, but was about 2.2-fold stabilized by Stabilon tagging. Flag-Oct4 (pseudogene) was about 10-fold stabilized by MG132, but was about 2.7-fold stabilized by Stabilon tagging. Flag-Sox2 was about 2.3-fold stabilized by MG132, but was about 15-fold stabilized by Stabilon tagging. Flag-Klf4 was about 3-fold stabilized by MG132, but was about 2.7-fold stabilized by Stabilon tagging. From these results, it was considered that a Stabilon tag has degradation resistance equal to or higher than that of MG132. Therefore, there is a possibility that fusion of Stabilon to a piPS cell inducer enables the construction of a piPS cell in an about one week.

Next, the relationship between the sequence of Stabilon and the intracellular stabilization of a protein was examined.

Experimental Method

HEK293 cells cultured in a D-MEM containing 10% FBS were transfected with Flag- or HA-tagged Oct4, Sox2 or Klf4 incorporated into a pcDNA3 vector, using Polyfect. After 24 hours of transfection, a proteasome inhibitor MG132 at a final concentration of 10 µM was added to dishes of individual experimental lanes 2. After 36 hours of transfection incubation, the cells were washed with a PBS buffer, and the protein was extracted with a TNE-N+buffer. The extract was equally aliquoted and developed by SDS-PAGE electrophoresis. After the electrophoresis was completed, the separated protein was transferred onto a PVDF membrane and then subjected to Western blotting analysis using an HRP-conjugated Flag antibody and a β-actin antibody. Chemi-Lumi One L (Nacalai Tesque) as a substrate of detection was exposed to a Hyperfilm (GE Healthcare), followed by detection. Quantification of the detected band was carried out using an ImageJ (NIH). The results are shown in FIG. 8.

Results

HA-Oct4 (WT) was about 1.7-fold stabilized by MG132, but was about 2.2-fold stabilized by Stabilon tagging. Flag-Oct4 (pseudogene) was about 10-fold stabilized by MG132, but was about 2.7-fold stabilized by Stabilon tagging. Flag-Sox2 was about 2.3-fold stabilized by MG132, but was about 15-fold stabilized by Stabilon tagging. Flag-Klf4 was about 3-fold stabilized by MG132, but was about 2.7-fold stabilized by Stabilon tagging. From these results, it was considered that a Stabilon tag has degradation resistance equal to or higher than that of MG132.

The invention claimed is:

1. A fusion protein which has an acquired proteolysis resistance, the fusion protein comprising an inducer for inducing a somatic cell into an induced pluripotent stem cell (iPS cell), the inducer being Oct4, Sox2, or Klf4, wherein a proteolysis-inhibiting motif is fused to at least one of the N-terminal and the C-terminal of the inducer, and wherein the proteolysis-inhibiting motif comprises the amino acid sequence of SEQ ID NO:1.

2. A pharmaceutical composition comprising the fusion protein according to claim 1.

3. The fusion protein according to claim 1, further comprising a cell membrane-permeable tag fused thereto.

4. A nucleic acid encoding the fusion protein according to claim 1.

5. An expression vector comprising the nucleic acid according to claim 4.

6. A transformant comprising the expression vector according to claim 5.

* * * * *

UNITED STATES PATENT AND TRADEMARK OFFICE
CERTIFICATE OF CORRECTION

| | | |
|---|---|---|
| PATENT NO. | : 9,079,968 B2 | Page 1 of 1 |
| APPLICATION NO. | : 13/321381 | |
| DATED | : July 14, 2015 | |
| INVENTOR(S) | : Shigemasa Hanazawa et al. | |

It is certified that error appears in the above-identified patent and that said Letters Patent is hereby corrected as shown below:

In the Claims

Claim 2, Column 28, Line 49 (Approximately)

Delete "pharmaceutical composition" and insert --composition--, therefor.

Signed and Sealed this
Thirteenth Day of October, 2015

Michelle K. Lee
*Director of the United States Patent and Trademark Office*

SEQUENCE LISTING

<160> NUMBER OF SEQ ID NOS: 30

<210> SEQ ID NO 1
<211> LENGTH: 16
<212> TYPE: PRT

-continued

```
<213> ORGANISM: Human

<400> SEQUENCE: 1

Glu Asp Asp Glu Glu Asp Asp Phe Asn Glu Asn Asp Glu Asp Asp
1               5                   10                  15

<210> SEQ ID NO 2
<211> LENGTH: 5
<212> TYPE: PRT
<213> ORGANISM: HUMAN

<400> SEQUENCE: 2

Glu Asp Asp Glu Glu
1               5

<210> SEQ ID NO 3
<211> LENGTH: 410
<212> TYPE: PRT
<213> ORGANISM: HUMAN

<400> SEQUENCE: 3

Met Ala Lys Asp Ala Gly Leu Ile Glu Ala Asn Gly Glu Leu Lys Val
1               5                   10                  15

Phe Ile Asp Gln Asn Leu Ser Pro Gly Lys Gly Val Val Ser Leu Val
                20                  25                  30

Ala Val His Pro Ser Thr Val Asn Pro Leu Gly Lys Gln Leu Leu Pro
            35                  40                  45

Lys Thr Phe Gly Gln Ser Asn Val Asn Ile Ala Gln Gln Val Val Ile
        50                  55                  60

Gly Thr Pro Gln Arg Pro Ala Ala Ser Asn Thr Leu Val Val Gly Ser
65                  70                  75                  80

Pro His Thr Pro Ser Thr His Phe Ala Ser Gln Asn Gln Pro Ser Asp
                85                  90                  95

Ser Ser Pro Trp Ser Ala Gly Lys Arg Asn Arg Lys Gly Glu Lys Asn
                100                 105                 110

Gly Lys Gly Leu Arg His Phe Ser Met Lys Val Cys Glu Lys Val Gln
            115                 120                 125

Arg Lys Gly Thr Thr Ser Tyr Asn Glu Val Ala Asp Glu Leu Val Ala
        130                 135                 140

Glu Phe Ser Ala Ala Asp Asn His Ile Leu Pro Asn Glu Ser Ala Tyr
145                 150                 155                 160

Asp Gln Lys Asn Ile Arg Arg Val Tyr Asp Ala Leu Asn Val Leu
                165                 170                 175

Met Ala Met Asn Ile Ile Ser Lys Glu Lys Lys Glu Ile Lys Trp Ile
            180                 185                 190

Gly Leu Pro Thr Asn Ser Ala Gln Glu Cys Gln Asn Leu Glu Val Glu
        195                 200                 205

Arg Gln Arg Arg Leu Glu Arg Ile Lys Gln Lys Gln Ser Gln Leu Gln
        210                 215                 220

Glu Leu Ile Leu Gln Gln Ile Ala Phe Lys Asn Leu Val Gln Arg Asn
225                 230                 235                 240

Arg His Ala Glu Gln Gln Ala Ser Arg Pro Pro Pro Pro Asn Ser Val
                245                 250                 255

Ile His Leu Pro Phe Ile Ile Val Asn Thr Ser Lys Lys Thr Val Ile
            260                 265                 270

Asp Cys Ser Ile Ser Asn Asp Lys Phe Glu Tyr Leu Phe Asn Phe Asp
        275                 280                 285
```

```
Asn Thr Phe Glu Ile His Asp Asp Ile Glu Val Leu Lys Arg Met Gly
            290                 295                 300

Met Ala Cys Gly Leu Glu Ser Gly Ser Cys Ser Ala Glu Asp Leu Lys
305                 310                 315                 320

Met Ala Arg Ser Leu Val Pro Lys Ala Leu Glu Pro Tyr Val Thr Glu
                325                 330                 335

Met Ala Gln Gly Thr Val Gly Gly Val Phe Ile Thr Thr Ala Gly Ser
                340                 345                 350

Thr Ser Asn Gly Thr Arg Phe Ser Ala Ser Asp Leu Thr Asn Gly Ala
            355                 360                 365

Asp Gly Met Leu Ala Thr Ser Ser Asn Gly Ser Gln Tyr Ser Gly Ser
        370                 375                 380

Arg Val Glu Thr Pro Val Ser Tyr Val Gly Glu Asp Glu Glu Asp
385                 390                 395                 400

Asp Asp Phe Asn Glu Asn Asp Glu Asp
                405                 410

<210> SEQ ID NO 4
<211> LENGTH: 8
<212> TYPE: PRT
<213> ORGANISM: Artificial
<220> FEATURE:
<223> OTHER INFORMATION: Flag tag

<400> SEQUENCE: 4

Asp Tyr Lys Asp Asp Asp Asp Lys
1               5

<210> SEQ ID NO 5
<211> LENGTH: 38
<212> TYPE: DNA
<213> ORGANISM: Artificial
<220> FEATURE:
<223> OTHER INFORMATION: Forward primer used for Flag-DP-1 mRNA cloning

<400> SEQUENCE: 5
agagaaccca ctgcttactg gcttatcgaa attaatac                             38

<210> SEQ ID NO 6
<211> LENGTH: 35
<212> TYPE: DNA
<213> ORGANISM: artificial
<220> FEATURE:
<223> OTHER INFORMATION: Reverse primer used for Flag-DP-1 mRNA cloning

<400> SEQUENCE: 6
cgagcgggtt gacggtggag gggtgaacgg ccacg                                35

<210> SEQ ID NO 7
<211> LENGTH: 23
<212> TYPE: DNA
<213> ORGANISM: artificial
<220> FEATURE:
<223> OTHER INFORMATION: Forward primer used for GAPDH cloning

<400> SEQUENCE: 7
cccagaagac tgtggatggc ccc                                             23

<210> SEQ ID NO 8
<211> LENGTH: 32
<212> TYPE: DNA
<213> ORGANISM: artificial
```

-continued

```
<220> FEATURE:
<223> OTHER INFORMATION: Reverse primer used for GAPDH cloning

<400> SEQUENCE: 8
cgttgtcata ccaggaaatg agcttgacaa ag                                    32

<210> SEQ ID NO 9
<211> LENGTH: 35
<212> TYPE: DNA
<213> ORGANISM: artificial
<220> FEATURE:
<223> OTHER INFORMATION: 5'-Forward primer used for FlagDP-1(delta C364)
      cloning

<400> SEQUENCE: 9
tcgaattcat ggcaaaagat gccggtctaa ttgaa                                 35

<210> SEQ ID NO 10
<211> LENGTH: 37
<212> TYPE: DNA
<213> ORGANISM: artificial
<220> FEATURE:
<223> OTHER INFORMATION: 5'-Reverse primer used for FlagDP-1(delta C364)
      cloning

<400> SEQUENCE: 10
aattctagat cacagctcac tggcagagaa ccttgtg                               37

<210> SEQ ID NO 11
<211> LENGTH: 35
<212> TYPE: DNA
<213> ORGANISM: artificial
<220> FEATURE:
<223> OTHER INFORMATION: 5'-Forward primer used for Flag DP-1(delta
      C395) cloning

<400> SEQUENCE: 11
tcgaattcat ggcaaaagat gccggtctaa ttgaa                                 35

<210> SEQ ID NO 12
<211> LENGTH: 38
<212> TYPE: DNA
<213> ORGANISM: artificial
<220> FEATURE:
<223> OTHER INFORMATION: 5'-Reverse primer used for Flag DP-1(delta
      C395) cloning

<400> SEQUENCE: 12
aattctagat caccccccgac gtaggacacc ggagtctc                             38

<210> SEQ ID NO 13
<211> LENGTH: 35
<212> TYPE: DNA
<213> ORGANISM: artificial
<220> FEATURE:
<223> OTHER INFORMATION: 5'-Forward primer used for Flag DP-1(delta
      CTAD) cloning

<400> SEQUENCE: 13
tcgaattcat ggcaaaagat gccggtctaa ttgaa                                 35

<210> SEQ ID NO 14
<211> LENGTH: 37
<212> TYPE: DNA
<213> ORGANISM: artificial
<220> FEATURE:
<223> OTHER INFORMATION: 5'-Reverse primer used for Flag DP-1(delta
```

-continued

CTAD) cloning

<400> SEQUENCE: 14
aattctagat caccccgacg taggacaccg gagtctc         37

<210> SEQ ID NO 15
<211> LENGTH: 36
<212> TYPE: DNA
<213> ORGANISM: artificial
<220> FEATURE:
<223> OTHER INFORMATION: 5'-Forward primer used for Flag DP-1(delta
      N102) cloning

<400> SEQUENCE: 15
aagaattcaa gcgcaacagg aaaggagaga agaatg          36

<210> SEQ ID NO 16
<211> LENGTH: 34
<212> TYPE: DNA
<213> ORGANISM: artificial
<220> FEATURE:
<223> OTHER INFORMATION: 5'-Reverse primer used for Flag DP-1(delta
      N102) cloning

<400> SEQUENCE: 16
aattctagat cagtcgtcct cgtcattctc gttg            34

<210> SEQ ID NO 17
<211> LENGTH: 36
<212> TYPE: DNA
<213> ORGANISM: artificial
<220> FEATURE:
<223> OTHER INFORMATION: 5'-Forward primer used for Flag DP-1(delta
      N102+delta CTAD)

<400> SEQUENCE: 17
aagaattcaa gcgcaacagg aaaggagaga agaatg          36

<210> SEQ ID NO 18
<211> LENGTH: 37
<212> TYPE: DNA
<213> ORGANISM: artificial
<220> FEATURE:
<223> OTHER INFORMATION: 5'-Reverse primer used for Flag DP-1(delta
      N102+delta CTAD)

<400> SEQUENCE: 18
aattctagat caccccgacg taggacaccg gagtctc         37

<210> SEQ ID NO 19
<211> LENGTH: 36
<212> TYPE: DNA
<213> ORGANISM: artificial
<220> FEATURE:
<223> OTHER INFORMATION: 5'-Forward primer used for Flag DP-1(delta
      N126) cloning

<400> SEQUENCE: 19
aagaattcca gaggaaaggg accacttcct acaacg          36

<210> SEQ ID NO 20
<211> LENGTH: 34
<212> TYPE: DNA
<213> ORGANISM: artificial
<220> FEATURE:
<223> OTHER INFORMATION: 5'-Reverse primer used for Flag DP-1(delta
      N126) cloning

```
<400> SEQUENCE: 20
aattctagat cagtcgtcct cgtcattctc gttg                        34

<210> SEQ ID NO 21
<211> LENGTH: 36
<212> TYPE: DNA
<213> ORGANISM: artificial
<220> FEATURE:
<223> OTHER INFORMATION: 5'-Forward primer used for Flag DP-1(delta
      N126+delta CTAD)

<400> SEQUENCE: 21
aagaattcca gaggaaaggg accacttcct acaacg                      36

<210> SEQ ID NO 22
<211> LENGTH: 37
<212> TYPE: DNA
<213> ORGANISM: artificial
<220> FEATURE:
<223> OTHER INFORMATION: 5'-Reverse primer used for Flag DP-1(delta
      N126+delta CTAD)

<400> SEQUENCE: 22
aattctagat caccccgacg taggacaccg gagtctc                     37

<210> SEQ ID NO 23
<211> LENGTH: 28
<212> TYPE: DNA
<213> ORGANISM: artificial
<220> FEATURE:
<223> OTHER INFORMATION: 5'-Forward primer used for Flag DP-1(delta
      N191) cloning

<400> SEQUENCE: 23
aagaattcgg tctgcccacc aactcggc                               28

<210> SEQ ID NO 24
<211> LENGTH: 34
<212> TYPE: DNA
<213> ORGANISM: artificial
<220> FEATURE:
<223> OTHER INFORMATION: 5'-Reverse primer used for Flag DP-1(delta
      N191) cloning

<400> SEQUENCE: 24
aattctagat cagtcgtcct cgtcattctc gttg                        34

<210> SEQ ID NO 25
<211> LENGTH: 28
<212> TYPE: DNA
<213> ORGANISM: artificial
<220> FEATURE:
<223> OTHER INFORMATION: 5'-Forward primer used for Flag DP-1(delta
      N191+delta CTAD) cloning

<400> SEQUENCE: 25
aagaattcgg tctgcccacc aactcggc                               28

<210> SEQ ID NO 26
<211> LENGTH: 37
<212> TYPE: DNA
<213> ORGANISM: artificial
<220> FEATURE:
<223> OTHER INFORMATION: 5'-Reverse primer used for Flag DP-1(delta
      N191+delta CTAD) cloning
```

```
<400> SEQUENCE: 26
aattctagat caccccgacg taggacaccg gagtctc                              37

<210> SEQ ID NO 27
<211> LENGTH: 35
<212> TYPE: DNA
<213> ORGANISM: artificial
<220> FEATURE:
<223> OTHER INFORMATION: 5'-Forward primer used for Flag DP-1(delta
      C191-410) cloning

<400> SEQUENCE: 27
tcgaattcat ggcaaaagat gccggtctaa ttgaa                                35

<210> SEQ ID NO 28
<211> LENGTH: 42
<212> TYPE: DNA
<213> ORGANISM: artificial
<220> FEATURE:
<223> OTHER INFORMATION: 5'-Reverse primer used for Flag DP-1(delta
      C191-410) cloning

<400> SEQUENCE: 28
tttctagatt aaatccactt gatctccttc ttctccttgg ag                        42

<210> SEQ ID NO 29
<211> LENGTH: 35
<212> TYPE: DNA
<213> ORGANISM: artificial
<220> FEATURE:
<223> OTHER INFORMATION: 5'-Forward primer used for Flag DP-1(delta
      C127-410) cloning

<400> SEQUENCE: 29
tcgaattcat ggcaaaagat gccggtctaa ttgaa                                35

<210> SEQ ID NO 30
<211> LENGTH: 37
<212> TYPE: DNA
<213> ORGANISM: artificial
<220> FEATURE:
<223> OTHER INFORMATION: 5'-Reverse primer used for Flag DP-1(delta
      C127-410) cloning

<400> SEQUENCE: 30
tttctagatt acaccttctc gcagaccttc atggaga                              37
```